United States Patent
Cavalla et al.

(10) Patent No.: US 6,268,373 B1
(45) Date of Patent: Jul. 31, 2001

(54) TRISUBSTITUTED THIOXANTHINES

(75) Inventors: David Cavalla, Cambridge (GB); Peter Hofer, Liestal (CH); Mark Chasin, Manalapan, NJ (US)

(73) Assignee: Euro-Celtique S.A., Luxembourg (LU)

(*) Notice: Subject to any disclaimer, the term of this patent is extended or adjusted under 35 U.S.C. 154(b) by 0 days.

(21) Appl. No.: 09/361,196

(22) Filed: Jul. 26, 1999

Related U.S. Application Data

(63) Continuation of application No. 08/860,674, filed as application No. PCT/US95/16724 on Dec. 12, 1995, now Pat. No. 6,025,361, which is a continuation-in-part of application No. 08/476,262, filed on Jun. 7, 1995, now abandoned.

(51) Int. Cl.[7] .................. C07D 473/20; C07D 473/22; A61K 31/52; A61K 31/522; A61P 11/06

(52) U.S. Cl. .................. 514/263; 544/267; 544/273

(58) Field of Search ............... 544/273, 267; 514/263

(56) References Cited

U.S. PATENT DOCUMENTS

| | | | |
|---|---|---|---|
| 3,135,753 | 6/1964 | Hitchings et al. | 544/265 |
| 4,107,306 | * 8/1978 | Vorhees | 546/144 |
| 4,925,847 | 5/1990 | Hofer | 514/263 |
| 4,981,857 | 1/1991 | Daluge et al. | 514/263 |
| 5,068,236 | 11/1991 | Suzuki et al. | 514/263 |
| 5,177,085 | * 1/1993 | Naef | 546/144 |
| 5,714,494 | * 2/1998 | Connell | 544/268 |

FOREIGN PATENT DOCUMENTS

| | | | |
|---|---|---|---|
| 0178413 | 4/1986 | (EP) | C07D/235/18 |
| 430300 | * 5/1991 | (EP) | |
| 0470805 | 2/1992 | (EP) | C07C/271/60 |
| 0497564 | 8/1992 | (EP) | |
| 0511865 | 11/1992 | (EP) | |
| 835818 | 8/1960 | (FR) | |
| 1548252 | 12/1968 | (FR) | |
| 1077689 | 8/1967 | (GB) | C07D/473/00 |
| 1498705 | 1/1978 | (GB) | A61K/31/40 |
| 2041359 | 9/1980 | (GB) | C07D/473/34 |
| 9219594 | 11/1992 | (WO) | |
| 9307111 | 4/1993 | (WO) | |
| 9314082 | 7/1993 | (WO) | |
| 9315044 | 8/1993 | (WO) | |
| 9315045 | 8/1993 | (WO) | |
| 9319747 | 10/1993 | (WO) | |
| 9325517 | 12/1993 | (WO) | |
| 9402465 | 2/1994 | (WO) | |
| 9410118 | 5/1994 | (WO) | |
| 9412461 | 6/1994 | (WO) | |
| 9414742 | 7/1994 | (WO) | |
| 9414800 | 7/1994 | (WO) | |
| 9420446 | 9/1994 | (WO) | |
| 9420455 | 9/1994 | (WO) | |

OTHER PUBLICATIONS

Silver, Paul J., et al., "Differential Pharmacologic Sensitivity of Cyclic Nucleotide Phosphodiesterase Isozymes Isolated from Cardiac Muscle, Arterial and Airway Smooth Muscle," *European J. of Pharm.*, 1988, 150:85–94.

*Tetrahedron Letters*, 1982, 23(21):2203–2204. (Itaya et al).

Thompson, W. Joseph, et al., "Assay of Cyclic Nucleotide Phosphodiesterase and Resolution of Multiple Molecular Forms of the Enzyme," *Advances in Cyclic Nucleotide Research*, 1979, 10:69–92.

*Chemical Abstracts*, Feb. 14, 1977, 86(7):43746r. (Aida).

*Chemical Abstracts*, Jul. 5, 1976, 85(1):5692s. (Enoki).

*Chemical Abstracts*, Jun. 21, 1976, 84(25):180299v. (Enoki).

*Chemical Abstracts*, May 12, 1975, 82(19):125358X. (Kazimierezvk).

*Chemical Abstracts*, Aug. 16, 1971, 75(7):49027b, (Rogers).

Torphy, Theodore J., et al., "Novel Phosphodiesterase Inhibitors for the Therapy of Asthma," *DN & P*, May 1993, 6(4):203–214.

Torphy, Theodore J., et al., "Identification, Characterization and Functional Role of Phosphodiesterase Isozymes in Human Airway Smooth Muscle," *J. of Pharm. and Experimental Therapeutics*, 1993, 265(3):1213–1223.

Giembycz, Mark A., "Could Isoenzyme–Selective Phosphodiesterase Inhibitors Render Bronchodilator Therapy Redundant in the Treatment of Bronchial Asthma?", *Biochem. Pharm.*, 1992, 43(10):2041–2051.

Lowe, John A., III, et al., "The PDE IV Family of Calcium–Independent Phosphodiesterase Enzymes," *Drugs of the Future*, 1992, 17(9):799–807.

Torphy, Theodore J., et al., "Phosphodiesterase Inhibitors: New Opportunities for the Treatment of Asthma," *Thorax*, 1991, 46:512–523.

(List continued on next page.)

Primary Examiner—Mark L. Berch
(74) Attorney, Agent, or Firm—Davidson, Davidson & Kappel, LLC

(57) ABSTRACT

Disclosed is a compound selected from the group consisting of 1,3,8-triethyl-2,6-dithioxanthine; 1,3,8-triethyl-2-thioxanthine; 8-cyclopropyl-1-ethyl-3-(2-methyl-butyl)-6-thioxanthine; 1,3-diethyl-8-isopropyl-6-thioxanthine; 8-cyclopropyl-1,3-dipropyl-6-thioxanthine; 8-isopropyl-1,3-dipropyl-6-thioxanthine; 1,3-diethyl-8-cyclopropyl-2,6-dithioxanthine; 1-(4-chlorobenzyl)-3-ethyl-8-isopropyl-6-thioxanthine; and 8-cyclopropyl-1,3-diethyl-6-thioxanthine. Also disclosed is a pharmaceutical composition comprising at least one pharmaceutically acceptable carrier and a compound selected from the group above. Also disclosed is a method of effecting PDE IV inhibition which comprises administering to a patient suffering from a disease or disorder selected from the group consisting of asthma, allergies, PDE IV modulated inflammation, and depression, a therapeutically effective amount of a compound selected from the group above.

13 Claims, 1 Drawing Sheet

OTHER PUBLICATIONS

Nicholson, C. David, et al., "Differential Modulation of Tissue Function and Therapeutic Potential of Selective Inhibitors of Cyclic Nucleotide Phosphodiesterase Isoenzymes," *TIPS*, 1991, 12:19–27.

Armitage, A.K., et al., "Structure–Activity Relationships in a Series of 6–Thioxanthines with Bronchodilator and Coronary Dilator Properties," *Brit. J. of Pharm.*, 1961, 17:196–207.

Woolridge, K.R.H., et al., "The Synthesis of Some 6–Thioxanthines," *J. of Chem. Soc. Annex*, IV:1863–1868.

Weinberger, Miles, M.D., "The Pharmacology and Therapeutic Use of Theophylline," *J. of Allergy and Clin. Immunology*, 73(5)(1):525–544.

Bowden, Boichemical Pharmacology 22, 1015, 1973.*

* cited by examiner

TRISUBSTITUTED THIOXANTHINES

This application is a continuation of U.S. Ser. No. 08/860,674, filed Sep. 29, 1997, which is a 371 of PCT/US95/16724, filed Dec. 12, 1995, now issued as U.S. Pat. No. 6,025,361; which is a continuation-in-part of U.S. Ser. No. 08/476,262 filed Jun. 7, 1995 now abandoned.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., beta-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these actually may contribute to its activity, only PDE inhibition may account for both the anti-inflammatory and bronchodilatory components. However, theophylline is known to have a narrow therapeutic index, and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular (cAMP) or (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, anti-inflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which following structural formula:

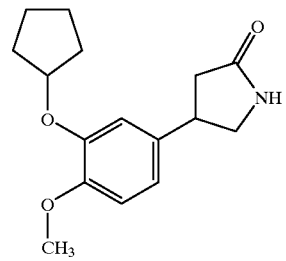

and of Ro-20-1724, which has the following structural formula:

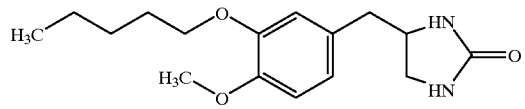

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Besides initial work suggesting an antidepressant action, rolipram has been investigated for its anti-inflammatory effects, particularly in asthma. In-vitro, rolipram, Ro-20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

Other PDE-IV inhibitors are 3,8-alkyl-disubstituted-6-thioxanthines disclosed by U.S. Pat. No. 4,925,847, issued May 15, 1990 to Hofer, the disclosure of which is incorporated by reference herein in its entirety.

PDE IV is present in all the major inflammatory cells in asthma including eosinophils, neutrophils, T-lymphocytes, macrophages and endothelial cells. Its inhibition causes down-regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammatory and bronchodilator activity without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids.

Additional thioxanthine compounds are known to the art. However, although some have been suggested to be useful for treating, e.g., asthma, the specific anti-PDE IV activity of these compounds has not been determined. For example, French Patent No. 188M, issued on Aug. 12, 1960 to May & Baker, Ltd, discloses the synthesis of the disubstituted thioxanthines 3-butyl-1-methyl-6-thioxanthine and 3-isobutyl-1-methyl-6-thioxanthine for bronchial or coronary artery dilation without disclosing any PDE IV inhibitory effects. French Patent No. 188M also discloses trisubstituted 6-thioxanthines (Formula I of the 188M patent) having at the 1 and 3 positions an alcohol or alkyl ($C_{1-6}$), straight or branched and H or an alcohol ($C_{1-6}$) at the 8 position.

Woolridge et al., 1962, J. Chem. Soc. Annex IV:1863–1868 discloses the synthesis of disubstituted 6-thioxanthines: 1,3 and 3,7-disubstituted 6-thioxanthines for bronchial or coronary dilation as well as 1,3,8 lower tri-alkyl substituted 6-thioxanthines where the alkyl groups are methyl or ethyl. PDE IV activity was uncharacterized.

Armitage et al., 1961, Brit. J. Pharm. 17:196–207, disclose trisubstituted 6-thioxanthines having bronchial and coronary dilator activity. The 1,3,8-trisubstituted 6-thioxanthines disclosed by Armitage are 1,3,8-trimethyl-6-thioxanthine and 1,3-dimethyl-8-ethyl-6-thioxanthine.

Some trisubstituted xanthine derivatives having diuretic, renal protective and vasodilator properties are disclosed by U.S. Pat. No. 5,068,236, issued to Suzuki et al. on Nov. 26, 1991. Suzuki et al. disclose xanthines, including trisubstituted xanthines having a lower alkyl independently at positions 1 and 3 and a —$CH_2$—($R^4$)$R^5$ at the 8 position, wherein $R^4$ and $R^5$ are independently substituted or unsubstituted alicyclic alkyl or substituted or unsubstituted aryl. The exemplified trisubstituted compounds having bronchial and coronary dilator activity are not characterized as to PDE IV activity.

Therefore, there remains a continuing need to find new thioxanthine compounds having more selective and improved PDE IV inhibitory activity.

OBJECTS AND SUMMARY OF THE INVENTION

It is according a primary object of the present invention to provide new compounds which are more effective selective PDE IV inhibitors.

It is another object of the present invention to provide new compounds which act as effective PDE IV inhibitors with lower PDE III inhibition.

It is a further object of the present invention to provide new compounds which have a superior PDE IV inhibitory effect as compared to theophylline, disubstituted 6-thioxanthines or other known compounds.

It is another object of the present invention to provide methods for treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, a disease caused by Human Immunodeficiency Virus and disease states associated with abnormally high physiological levels of cytokines.

Other objects and advantages of the present invention will become apparent from the following detailed description thereof.

With the above and other objects in view, the present invention comprises compounds of Formula I as follows.

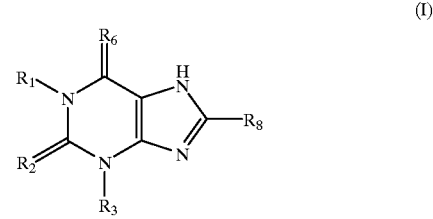

(I)

wherein:
$R^1$, $R^3$ and $R^8$ are independently selected from alkyl, aryl and aralkyl moieties,
$R^2$ and $R^6$ are independently S or O; with the exception that $R^2$ and $R^6$ are not both O.

In certain preferred embodiments, $R^1$ and $R^3$ are aralkyl; and $R^8$ is optionally cycloalkyl, aryl, aralkyl or an alkyl which is either straight or branched, such as methyl, ethyl, isopropyl, n-propyl, cyclopropyl, butyl and pentyl; and one of $R^1$ and $R^3$ is benzyl. Furthermore, the aryl groups can be substituted or unsubstituted.

Some particularly preferred compounds in accordance with the present invention include:
1,3-Di-(4-chlorobenzyl)-8-isopropyl-thioxanthine;
3-(3-Cyclopentyloxy-4-methoxy-benzyl)-1-ethyl-8-isopropyl-6-thioxanthine;
1,3-diethyl-8-cyclopropyl-2,6-dithioxanthine; and
1,3-diethyl-8-(isopropyl)-6-thioxanthine.

The invention also comprises pharmaceutical compositions including an effective amount of a compound according to Formula (I), or a salt thereof, together with a pharmaceutically acceptable carrier. The pharmaceutically acceptable carrier is suitable for administration of the pharmaceutical composition orally, topically, by suppository, inhalation, insufflation, and parenterally and any other suitable method for administering a medication.

The invention also provides methods for selectively inhibiting PDE IV and/or PDE V enzyme activity in a patient requiring the same by administering a compound according to the invention by administering an effective amount of a pharmaceutically acceptable compound according to the invention.

Alternatively, the invention provides methods for treating a patient suffering from a disease or disorder such as asthma, allergies, inflammation, depression, dementia, atopic diseases, rhinitis and disease states associated with abnormally high physiological levels of cytokine by administering an effective amount of a pharmaceutically acceptable compound according to the invention.

Both methods comprise administering an effective amount of the compound according to Formula (I) in a pharmaceutically acceptable form as described above to a patent in need of such treatment.

In preferred aspects of the invention, the method includes administering one of the following compounds:

1,3,8-triethyl-2,6dithioxanthine;
1,3,8-triethyl-2-thioxanthine;
8-cyclopropyl-1-ethyl-3-(2 methyl butyl) 6-thioxanthine;
1,8-diethyl-3-(2-methylbutyl)-6-thioxanthine;
3-ethyl-1-methyl-8-isopropyl-6-thioxanthine;
1,3-diethyl-8-(isopropyl)-6-thioxanthine;
8-cyclopropyl-1,3-dipropyl-6-thioxanthine;
8-ethyl-1,3-dipropyl-thioxanthine;
8-isopropyl-1,3-dipropyl-6-thioxanthine;
1,3-diethyl-8-cyclopropyl-2,6-dithioxanthine;
1,3-di-(4-chlorobenzyl)-8-isopropyl-6-thioxanthine;
3-(3-cyclopentyloxy-4-methoxy-benzyl)-1-ethyl-8-isopropyl-6-thioxanthine;
1-(4-chlorobenzyl)-3-ethyl-8-isopropyl-6-thioxanthine; and
3-(4-chlorobenzyl)-1-ethyl-8-isopropyl-6-thioxanthine.

An alternative aspect of the invention includes a method of treatment which involves administering an effective amount of a pharmaceutically acceptable compound according to the invention having anti-inflammatory and/or immunosuppressant activity, to a patient in need of such treatment.

When $R^1$ and $R^3$ of the compound are independently aryl, or arylalkyl and have bronchodilator activity, the method of treatment according to the invention involves administering the compound to a patient in need of such treatment.

DETAILED DISCLOSURE OF THE INVENTION

Figure 1:
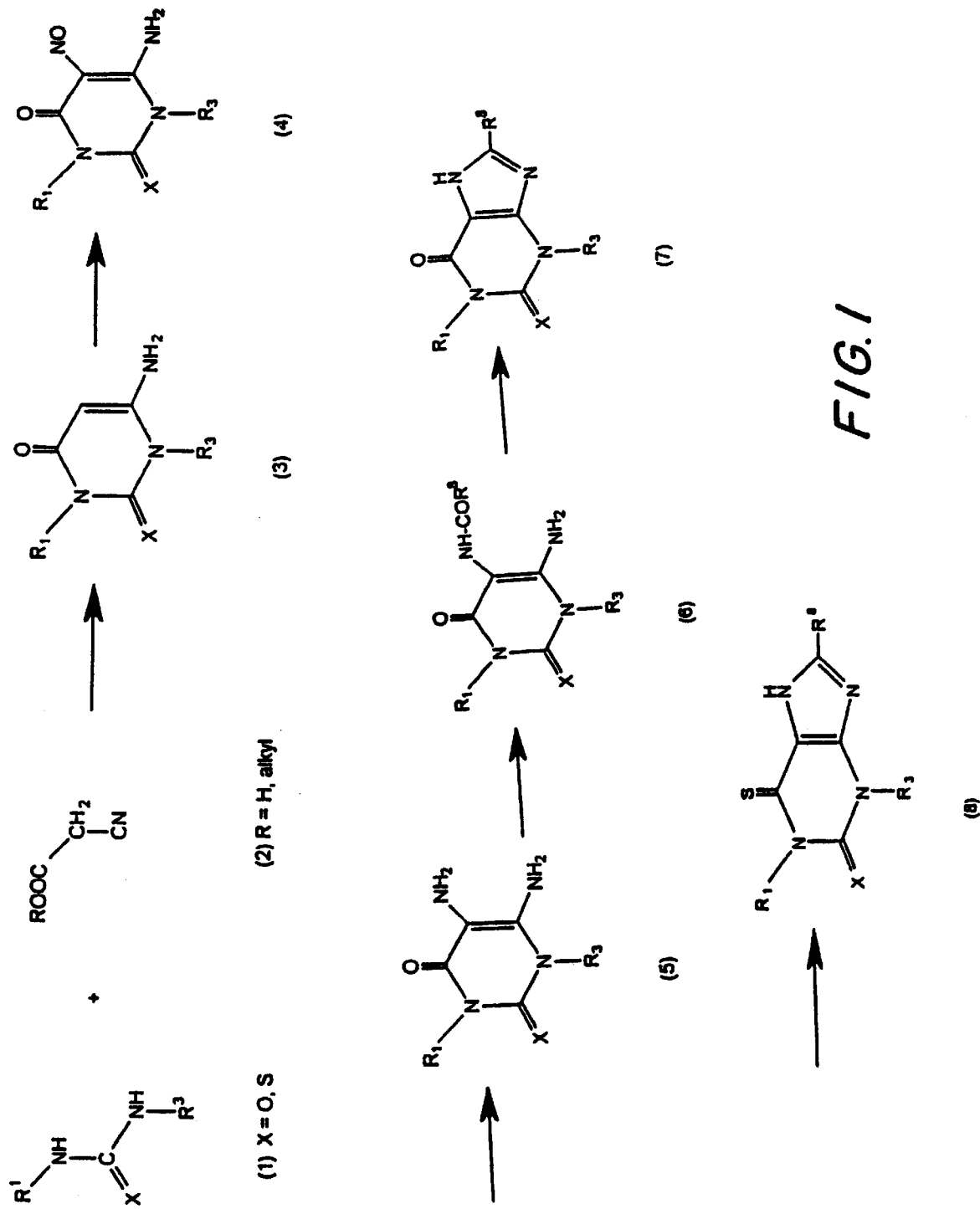
FIG. 1 provides reaction scheme 1 exemplifying preparation of certain compounds according to the invention.

The compounds of the present invention, as demonstrated in the appended examples, are effective in the mediation or inhibition of PDE IV enzyme activity in need of such treatment. Further, these compounds are selective PDE IV inhibitors which possess bronchodilatory, anti-inflammatory and other properties characteristic of PDE IV inhibitors substantially without undesirable cardiovascular stimulation caused by PDE III inhibition. Many of these compounds have a substantially equal or superior PDE IV inhibitory effect as compared to theophylline, disubstituted 6-thioxanthines and other previously known PDE IV inhibitors.

Accordingly the present invention provides novel compounds having unexpectedly superior PDE IV inhibitory activity and novel methods for treating diseases or disorders related to PDE IV enzyme activity. The compounds according to the invention mainly comprise compounds of Formula I below:

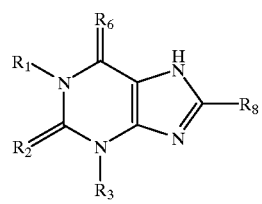

(I)

wherein:
$R^1$, $R^3$ and $R^8$ are independently selected from alkyl, aryl and aralkyl moieties,
$R^2$ and $R^6$ are independently S or O;
with the exception that $R^2$ and $R^6$ are not both O.

In certain preferred embodiments, $R^1$ and $R^3$ are independently an aralkyl, substituted or unsubstituted; and $R^8$ is optionally cycloalkyl, aryl, aralkyl or an alkyl which is either straight or branched, such as methyl, ethyl, isopropyl, n-propyl, cyclopropyl, butyl and pentyl; and one of $R^1$ and $R^3$ is benzyl.

$R^1$, $R^3$ and $R^8$ are optionally substituted by halogen, hydroxy, hydroxy, $C_1$–$C_4$ alkoxy, $C_3$–$C_7$ cycloalkoxy, oxo, oximido, carbamido or hydroxycarbimido.

In still further embodiments, one or more of $R^1$, $R^3$ and $R^8$ cycloalkylalkyl, preferably, in this embodiment, both $R^1$ and $R^3$ are cycloalkylalkyl moieties.

The alkyl moieties can be straight, branched or cyclic. $R^1$, $R^3$ and $R^8$ may have substituents such as halogen, hydroxy, $C_1$–$c_4$ alkoxy, $C_3$–$C_7$ cycloalkoxy, oxo, oximido, carbamido or hydroxycarbimido. Preferable alkyl moieties include straight or branched lower alkyls such as methyl, ethyl, isopropyl, n-propyl, cyclopropyl, butyl and pentyl. The alkyl portion of the aralkyl moieties is preferably a lower alkyl. The term "lower alkyl" is defined for purposes of the present invention as straight or branched chain radicals having from 1 to 8 carbon atoms. In one embodiment, $R^8$ is propyl and, preferably is isopropyl.

In another preferred embodiment, a compound of the present invention is one of the following:
1,3-Di-(4-chlorobenzyl)-8-isopropyl-6-thioxanthine;
3-(3-Cyclopentyloxy-4-methoxy-benzyl)-1-ethyl-8-isopropyl-6-thioxanthine;
1,3-diethyl-8-cyclopropyl-2,6-dithioxanthine; and
1,3-diethyl-8-(isopropyl)-6-thioxanthine.

The invention also provides for methods of selectively inhibiting the enzymes PDE IV and/or PDE V in a patient, in order to treat a disease or disorder related to elevated PDE IV and/or PDE V activity in a patient as enumerated above. The method of treatment comprises administering to a patient in need thereof an effective dose of a pharmacological active compound having PDE IV and/or PDE V inhibitory activity and a structure according to Formula I, supra.

In one embodiment, $R^1$ is a $C_{1-3}$ alkyl, straight or branched, $R^3$ is a $C_{1-5}$ alkyl, straight or branched and $R^8$ is an ethyl or propyl, including cyclopropyl and isopropyl, moiety In another embodiment, $R^1$ and $R^3$ are aralkyl, substituted or unsubstituted and $R^2$ and $R^6$ are S or O, but $R^2$ and $R^6$ are not both O and $R^8$ is alkyl or cycloalkyl, aryl or aralkyl, substituted or unsubstituted. Preferably, $R^8$ is propyl and more preferably, isopropyl.

The present invention is further related to a method for the treatment of allergic and inflammatory disease which comprises administering to a patient in need thereof an effective amount of the compounds of the present invention able to selectively inhibit PDE IV.

The compounds of the present invention may find use in the treatment of other diseases or disorders, such as, for example, in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

In a particular embodiment, the method of treatment involves administering compounds of the present invention having anti-inflammatory and/or immunosuppressants to a patient in need of such treatment.

In another particular embodiment, the method of treatment involves administering a compound of the present invention, wherein $R^1$ and $R^2$ are independently aryl or arylalkyl, to a patient in need of such treatment.

Within the formula set forth above, the following compounds are particularly preferred:

1,3,8-triethyl-2,6-dithioxanthine;
1,3,8-triethyl-2-thioxanthine;
8-cyclopropyl-1-ethyl-3-(2 methyl butyl) 6-thioxanthine;
1,8-diethyl-3-(2-methylbutyl)-6-thioxanthine;
3-ethyl-1-methyl-8-isopropyl-thioxanthine;
1,3-diethyl-8-isopropyl-6-thioxanthine;
8-cyclopropyl-1,3-dipropyl-6-thioxanthine;
8-ethyl-1,3-dipropyl-6-thioxanthine;
8-isopropyl-1,3-dipropyl-6-thioxanthine;
1,3-diethyl-8-cyclopropyl-2,6-dithioxanthine
1,3-Di-(4-chlorobenzyl)-8-isopropyl-6-thioxanthine
3-(3-Cyclopentyloxy-4-methoxy-benzyl)-1-ethyl-8-isopropyl-6-thioxanthine
1-(4-chlorobenzyl)-3-ethyl-8-isopropyl-6-thioxanthine; and
3-(4-chlorobenzyl)-1-ethyl-8-isopropyl-6-thioxanthine.

The compounds of the present invention have been found to be highly effective PDE IV inhibitors, the inhibition of which is in fact significantly and surprisingly greater than that of, for example, theophylline or disubstituted 6-thioxanthines.

In Example 14 there is provided a comparison of analogous disubstituted and trisubstituted xanthines which illustrate the advantages of trisubstituted xanthines. The trisubstituted compounds according to the invention have substantially lower PDE IV $IC_{50}$ values, indicating that these compounds will have increased potency and/or selectivity in the treatment of PDE IV related diseases or disorder.

A description of the synthesis of exemplary representatives of these molecules is set forth in the Examples. The synthesis of other molecules not specifically shown in the examples but within the scope of the invention are carried out using those techniques shown with modifications which are known to those of ordinary skill in the art. An overview of representative synthetic plans is provided by FIG. 1.

Turning now to the FIGURE, thioxanthines (8) can be prepared, for example, by two different routes, either starting with a N,N'-disubstituted(thio)urea, which can be applied for $R^1 \leq R^3$, or starting with a monosubstituted urea followed by alkylation of compounds of (6) where $R^1$ is H, 3,8-disubstituted thioxanthines with $R^3$=H, which can be applied in all cases, including $R^1 > R^3$. In Scheme 1, compound (1) (FIG. 1), where X=O, S, is reacted with compound (2), where R=H or alkyl, to produce compound (3). Steps (4) through (7) provide closure of the second aromatic ring to produce a xanthine where $R^6$ is O. Reactions producing compounds (7) through (8) provide a 6-thioxanthine as compound (8).

In FIG. 1, Scheme 1, thioxanthines can be prepared, for example, by two different routes, either starting with an N,N¹-disubstituted (thio)urea, which can be used for $R^1 \leq R^3$ or starting with a monosubstituted (thio)urea followed by alkylation of compounds of type (4) or (6) where $R^1$ is H, which can be applied in all cases, including $R^1 > R^3$. In scheme 1, compound (1), where X is O or S, is reacted with compound (2), where $R^1$ is H or other substituents, to produce compound (3). Steps (4) to (7) provide closure of the second ring to produce a xanthine where $R^6$ is O. Reactions producing compound (8) provide a 6-thioxanthine.

The present invention also encompasses, where appropriate, all pharmaceutically acceptable salts of the foregoing compounds. One skilled in the art will recognize that amine, alkali and alkaline earth metal salts are prepared by reaction of the compounds of the invention with the appropriate base via a variety of known methods.

The compounds of the present invention can be administered to anyone requiring PDE IV inhibition. Administration may be orally, topically, by suppository, inhalation or insufflation, or parenterally.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems.* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

In addition, the PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENT

The following examples illustrate various aspects of the present invention, and are not to be construed to limit the claims in any manner whatsoever.

EXAMPLE 1

1,3-Diethyl-8-cyclopropyl-2,6-dithioxanthine

A. 1,3-Diethyl-8-cyclopropyl-2-thioxanthine 25.1 g (100 mM) of 5,6-diamino 1,3-diethyl-2-thiouracil HCl were dissolved in 400 ml of pyridine, 12.72 g (120 mM) of sodium carbonate added, and under cooling a solution of 10.77 ml (120 mM) of cyclopropane carbonyl chloride in 50 ml of dried ether added within 10 minutes. After 20 min the solvents were evaporated in vacuo. The residue was treated with 200 ml of water and about 50 ml were removed again in vacuo. The suspension was diluted with 100 ml of 2N aqueous sodium hydroxide (NaOH) and heated under reflux for 30 minutes. A further 80 ml was distilled off during this time. After cooling the solution was acidified with 5N aqueous hydrochloric acid (HCl) to pH 5.5; 200 ml of water was added and the resulting suspension filtered. The solid was collected and washed, redissolved in 200 ml of 1N NaOH, treated twice with 0.4 g of charcoal, filtered and acidified again to pH 4.5. The solid was collected again, washed and dried to give 25.5 g of a solid which was suspended in 400 ml of hot methanol. The solid was collected again, washed and dried to give 23.5 g (89.0%) of 2-thioxanthine with mp subl. 265–7° C.

B. 1,3-diethyl-8-cyclopropyl-2,6-dithioxanthine 13.22 g (50 mM) of 2-thioxanthine and 13.34 g (60 mM) of phosphorus pentasulfide were heated under reflux in 160 ml of pyridine for 3 days. At 5–10° C., 66 ml (132 mM) of 2N NaOH were added. The solvents were evaporated in vacuo, the residue treated with 200 ml of water and evaporated again. The residue was again suspended in 200 ml of water and collected. The crude product was dissolved in 120 ml of 1N NaOH, treated twice with 0.14 g of charcoal, filtered and acidified with 32 ml of 5N HCl to pH 4.5. The solid was collected, washed and dried to give 14.31 g of crude dithioxanthine. This was dissolved in 300 ml of chloroform; some insoluble material was filtered off, and the solution passed through 71.5 g of silica gel in a column. Crystallization from isopropanol gave 12.17 g (86.8%) of 2,6-dithioxanthine with mp 196–200° C.

| Elemental analysis for $C_{12}H_{16}N_4S_2$: | | | | |
|---|---|---|---|---|
| Calculated: | C 51.40 | H 5.75 | N 19.98 | S 22.87 |
| Found: | C 51.87 | H 5.88 | N 20.33 | S 22.61 |

EXAMPLE 2

3-(4-Chlorobenzyl)-1-ethyl-8-isopropyl-6-thioxanthine

A. 3-(4-Chlorobenzyl)-1-ethyl-8-isopropyl-xanthine 13.47 g (40 mM) of 6-amino-1-(4-chlorobenzyl)-5-isobutyrylaminouracil were dissolved in 130 ml of DMF, treated at 5° C. with 4.57 g (40.8 mM) potassium t-butoxide and after dissolution, 3.28 ml (44 mM) of ethyl bromide added. After 3 hours, another 1.14 g of t-BuOK and 1.64 ml of ethyl bromide were added. After a further 1.5 hours, 1.64 ml of ethyl bromide was supplemented. After a total of 22 hours, the solution was neutralized with 1N HCl to pH 7 and the solvents evaporated in vacuo. The residue was taken up in dichloromethane-water and the organic phase collected giving 17.66 of crude 3-ethyl uracil, which was dissolved in 17.6 ml of 1N NaOH and heated under reflux for 1 hour. The solution was treated twice with 1 g of charcoal, filtered and neutralized with 5N HCl to pH 7. The solid was diluted with water, collected, and dried. The crude material was recrystallized from methanol to give 7.42 g (49.2%) of 3-(4-chlorobenzyl)-1-ethyl-8-isopropyl-xanthine, mp 221–2° C.

B. 3-(4-Chlorobenzyl)-1-ethyl-8-isopropyl-6-thioxanthine 6.59 g (19 mM) of xanthine and 5.07 g (22.8 mM) of phosphorus pentasulfide were heated under reflux in 102 ml of pyridine for 3 days. At 0° C., 25.1 ml of 2N NaOH were added. The solid was filtered off and washed with pyridine. The solvents were evaporated in vacuo, the residue suspended in water, collected, redissolved in 100 ml of 1N NaOH and 50 ml of isopropanol, treated twice with 0.3 g of charcoal, filtered and neutralized with 5N HCl to pH 7. The isopropanol was removed in vacuo and the solid collected, washed and dried to give 6.80 g (98.7%) of 6-thioxanthine, mp 188–9° C.

| Elemental analysis for $C_{17}H_{19}ClN_4OS$: | | | | |
|---|---|---|---|---|
| Calculated: | C 56.27 | H 5.28 | N 15.44 | O 4.41 |
| Found: | C 56.25 | H 5.33 | N 15.47 | O 4.41 |

EXAMPLE 3

1-(4-Chlorobenzyl)-3-ethyl-8-isopropyl-6-thioxanthine

A. 1-(4-Chlorobenzyl)-3-ethyl-8-isopropyl-xanthine 3.17 g (28.2 mM) of potassium t-butoxide (t-BuOK) were added to a solution of 6.11 g (27.5 mM) of 6-amino-1-ethyl-5-isobutyrylamino-uracil. At 0° C., 4.90 g (30.4 mM) of 4-chlorobenzylchloride were added. After 3 hours at 0–5° C., further 1.22 g t-BuOK and 2.45 g of 4-chlorobenzylchloride were added. After further 3 hours another 2.45 g of benzylchloride are supplemented. After 3 days, the solution was neutralized with 1N HCl and the solvents evaporated. The residue was suspended in water, the solid collected and washed. The crude intermediate amide was heated under reflux in 100 ml of 1N NaOH and 10 ml of 1-propanol. After 1 hour, the mixture was neutralized to pH 7 and extracted with chloroform. Crystallization from dichloromethane (mainly evaporated)-methanol gave 2.99 g (31.3%) of the title xanthine, mp 194–5° C. The mother liquors gave 6.33 g of impure material which was separated on 15 g of silica gel elutions with dichloromethane and gave additional 0.78 g (8.2%) of the xanthine.

B. 1-(4-Chlorobenzyl)-3-ethyl-8-isopropyl-thioxanthine 2.77 g (8.0 mM) of xanthine and 2.13 g (9.6 mM) of phosphorus pentasulfide were heated under reflux in 50 ml of pyridine for 7 days. At 0° C., 10.6 ml of 2N NaOH were added within 15 minutes. The solvents were evaporated in vacuo and the residue suspended (slow crystallization) in water. The solid was collected and washed, redissolved in 50 ml of 1N NaOH and 50 ml of isopropanol, treated twice with 0.3 g of charcoal, filtered neutralized with 5N HCl to pH 7. The isopropanol was distilled off with addition of water and the solid collected, washed and dried to give 2.60 g (89.7%) of crude thioxanthine, which was dissolved in 40 ml of dichloromethane and filtered through 30 g of silica gel: 1.91 g (65.9%) of 6-thioxanthine were recovered, mp 153–4° C.

EXAMPLE 4

1,3-8-Triethyl-2,6-dithioxanthine and 1,3,8-triethyl-2-thioxanthine

Using a process analogous to that used for Example 1, 1,3,8-triethyl-2,6-dithioxanthine and 1,3,8-triethyl-2-thioxanthine were prepared. A recrystallized sample from ether for the first compound had m.p. 144–6° C. while the second compound had a m.p. of 255–6° C.

| Elemental analysis for $C_{11}H_{16}N_4S_2$. | | | | |
|---|---|---|---|---|
| calc. | C 49.22 | H 6.01 | N 20.87 | S 23.89 |
| found | C 49.55 | H 6.11 | N 20.92 | S 23.83 |

EXAMPLE 5

1,3-Diethyl-8-isopropyl-6-thioxanthine 1,3-diethyl-8-isopropyl-xanthine (6.25 g, 25 mM) (J Amer Chem Soc 1953,75, 114–5) and 6.8 g (30 mM) of phosphorus pentasulfide were refluxed in 86 ml of pyridine for 3 days. At 10–20° C., 33.5 ml of 2N NaOH are added with cooling. The solid was filtered off and washed with pyridine. The filtrate was evaporated in vacuo to dryness, the residue suspended in 50 ml of water, adjusted to pH 7.5, the solid collected, washed with water and dried. The product was redissolved in 30 ml NaOH, treated twice with 0.5 g of charcoal, filtered, and acidified with 5N HCl to pH 3. At 5° C., the solid was collected, washed and dried. The compound had a mp of 168–70° C.

| Elemental analysis for $C_{12}H_{18}N_4OS$. | | | | |
|---|---|---|---|---|
| calc. | C 54.12 | H 6.81 | N 21.04 | S 12.04 |
| found | C 54.60 | H 6.94 | N 21.27 | S 12.12 |

EXAMPLE 6

1,3-Dipropyl-8-isopropyl-6-thioxanthine

Using a process analogous to that used for Example 5, 1, 3-dipropyl-8-isopropyl-6-thioxanthine were prepared, with a yield of 97.2%. A recrystallized sample from methanol had mp 133–4° C.

EXAMPLE 7

8-Cyclopropyl-1,3-dipropyl-6-thioxanthine

Using a process analogous to that of Example 5, 8-cyclopropyl-1,3-dipropyl-6-thioxanthine was prepared with a mp of 170–2° C. The yield was 94.3%.

| Elemental analysis for $C_{14}H_{20}N_4OS$. | | | | |
|---|---|---|---|---|
| calc. | C 57.51 | H 6.89 | N 19.16 | S 10.97 |
| found | C 57.38 | H 6.99 | N 19.26 | S 10.92 |

EXAMPLE 8

8-Cyclopropyl-1-ethyl-3-(2-methyl-butyl)-6-thioxanthine

Using a process analogous to that of Example 5, 8-cyclopropyl-1-ethyl-3-(2-methyl-butyl)-6-thioxanthine) was prepared with an mp of 147–8° C. Yield was 85.4%.

| Elemental analysis for $C_{15}H_{22}N_4OS$. | | | | |
|---|---|---|---|---|
| calc. | C 58.79 | H 7.24 | N 18.28 | S 10.46 |
| found | C 58.89 | H 7.34 | N 18.29 | S 10.76 |

EXAMPLE 9

1,8-Diethyl-3-(2-methyl-butyl)-6-thioxanthine

Using a process analogous to that of Example 5, 8-cyclopropyl-1-ethyl-3-(2-methyl-butyl)-6-thioxanthine) was prepared with a mp of 115–7° C. with a mp 170–2° C. Yield was 97.8%.

| Elemental analysis for $C_{14}H_{22}N_4OS$. | | | | |
|---|---|---|---|---|
| calc. | C 57.11 | H 7.53 | N 19.03 | S 10.89 |
| found | C 57.18 | H 7.67 | N 19.19 | S 10.76 |

EXAMPLE 10

1,3-Di-(4-chlorobenzyl)-8-isopropyl-6-thioxanthine

A. 1,3Di-(4-chlorobenzyl)-8-isopropyl-6-xanthine

Using a process analogous to Example 3, part a, 1,3-di-(4-chlorobenzyl)-8-isopropyl-6-xanthine was prepared. The yield of crude product was 96.5%. Crystallization from chloroform with a little methanol gave 59.8% yield of xanthine with mp 218–9° C.

B. 1,3-Di-(4-chlorobenzyl)-8-isopropyl-6-thioxanthine

Using a process analogous to Example 3, part b, 1,3-di-(4-chlorobenzyl)-8-isopropyl-6-thioxanthine was prepared. The yield of crude product was 87.1%. After filtration through silica gel and recrystallization from dichloromethane with a little methanol the yield obtained was 71.1% of thioxanthine with a mp 106–7/178° C.

| Elemental analysis for $C_{14}H_{22}N_4OS$. | | | | |
|---|---|---|---|---|
| calc. | C 55.35 | H 4.64 | N 11.74 | S 6.70 ($H_2O$) |
| found | C 55.54 | H 4.63 | N 11.83 | S 6.49 |

EXAMPLE 11

3-(3-Cyclopentyloxy-4-methoxy-benzyl)-1-ethyl 8-isopropyl-6-thioxanthine

A. 3-(3-Cyclopentyloxy-4-methoxy-benzyl)-1-ethyl-8-isopropyl-xanthine

Using a process analogous to that of Example 2, part a, 3-(3-cyclopentyloxy-4-methoxy-benzyl)-1-ethyl-8-isopropyl-xanthine was prepared with a yield of 63.3% and with mp 208–9° C.

B. 3-(3-Cyclopentyloxy-4-methoxy-benzyl)-1-ethyl-8-isopropyl-6-thioxanthine

Using a process analogous to Example 2, part b, with the modification that the refluxing step was conducted for 13 days, 3-(3-cyclopentyloxy-4-methoxy-benzyl)-1-ethyl-8-isopropyl-6-thioxanthine was prepared with a yield of 14.70%, m.p. 176–7° C.

| Elemental analysis for $C_{23}H_{30}N_4O_3S$. | | | | |
|---|---|---|---|---|
| calc. | C 62.42 | H 6.83 | N 12.66 | O 10.85 | S 7.24 |
| found | C 62.63 | H 6.93 | N 12.62 | O 10.99 | |

EXAMPLE 12

Following a procedure similar to that set forth in Example 1, the following 6-thioxanthines were prepared:

a) 3-Ethyl-8-isopropyl-1-methyl-thioxanthine; m.p.230–40° C.

| Elemental analysis for $C_{11}H_{16}N_4OS$ | | | |
|---|---|---|---|
| calc. | C 52.36 | H 6.39 | N 22.20 | S 12.71 |
| found | C 52.46 | H 6.34 | N 22.04 | S 12.74. | b) 1,3,8-Triethyl-6-thioxanthine; m.p. 176–8° C.

| Elemental analysis for $C_{11}H_{16}N_4OS$ | | | |
|---|---|---|---|
| calc. | C 52.36 | H 6.39 | N 22.20 | S 12.71 |
| found | C 52.75 | H 6.57 | N 22.39 | S 12.91 | c) 8-Cyclopropyl-1,3-diethyl-6-thioxanthine; m.p. 212–4° C.

| Elemental analysis for $C_{12}H_{16}N_4OS$ | | | |
|---|---|---|---|
| calc. | C 54.52 | H 6.10 | N 21.20 | S 12.13 |
| found | C 54.61 | H 6.24 | N 21.33 | S 12.15 | d) 1,3-dipropyl-8-ethyl-6-thioxanthine; m.p. 144–5° C.

| Elemental analysis for $C_{13}H_{20}N_4OS$ | | | |
|---|---|---|---|
| calc. | C 55.70 | H 7.19 | N 19.99 | S 11.42 |
| found | C 55.65 | H 7.33 | N 20.39 | S 11.38 | e) 1,8-dimethyl-3-(2-methylbutyl)-6-thioxanthine; m.p. 145–6° C.

| Elemental analysis for $C_{12}H_{18}N_4OS$ | | | |
|---|---|---|---|
| calc. | C 54.11 | H 6.81 | N 21.03 | S 12.04 |
| found | C 54.33 | H 6.93 | N 21.41 | S 12.08 |

EXAMPLE 13

Protocols for PDE IV inhibition activity are set forth below:

Type IV Phosphodiesterase Enzyme Isolation Protocol

The Type IV PDE is isolated from bovine tracheal smooth muscle using a procedure similar to that previously described by Silver, P. J. et al., Eur. J. Pharmacol. 150:85, 1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 mM, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

EXAMPLE 14

Comparison of PDE IV $IC_{50}$ Activity for Trisubstituted Thioxanthines and Disubstituted Thioxanthines The procedures of Example 13 were used to measure PDE IV activity for exemplary compounds and for some analogous disubstituted thioxanthine compounds in order to demonstrate the improved PDE IV $IC_{50}$ activity for the compounds according to the invention. The results, wherein a lower PDE IV $IC_{50}$ number indicates a superior activity, are provided below.

PDE IV INHIBITORY ACTIVITY

| Compound | PDE IV $IC_{50}$ ($\mu$M) |
|---|---|
| 8-cyclopropyl-1-ethyl-3-(2 methyl-butyl) 6-thioxanthine | 1.18 |
| 8-cyclopropyl-3-(2-methyl-butyl)-6-thioxanthine | 3.83* |
| 3-ethyl-8-isopropyl-6-thioxanthine | 4.6* |
| 3-ethyl-1-methyl-8-isopropyl-thioxanthine | 1.0 |
| 1,3-diethyl-8-isopropyl- 6-thioxanthine | 1.2 |
| 8-cyclopropyl-3-propyl-6-thioxanthine | 4.47* |
| 8-cyclopropyl-1,3-dipropyl-6-thioxanthine | 2.97 |
| 3-propyl-8-ethyl-6-thioxanthine | 18.37* |
| 8-isopropyl-3-propyl-6-thioxanthine | 3.3* |
| 8-isopropyl-1,3-dipropyl-6-thioxanthine | 1.67 |

*Disubstituted analog.

As indicated by the results shown by above, the trisubstituted alkyl thioxanthines demonstrate an improvement in PDE IV $IC_{50}$ activity over disubstituted analogs.

Separately, the PDE IV inhibitory $IC_{50}$'s for compounds of Example 12 were determined and are set forth below:

PDE IV INHIBITORY ACTIVITY

| Compound | PDE IV $IC_{50}$ ($\mu$M) |
|---|---|
| 3-Ethyl-8-isopropyl-1-methyl-6-thioxanthine | 1.0 |
| 8-Cyclopropyl-1,3-diethyl-6-thioxanthine | 1.4 |
| 1,3-dipropyl-8-ethyl-6-thioxanthine | 5.1 |
| 1,8-dimethyl-3-(2-methylbutyl)-6-thioxanthine | 7.1 |

EXAMPLE 15

Type V Phosphodiesterase Enzyme Isolation Protocol

Enzyme Isolation Procedure: The Type V PDE is isolated using a procedure similar to that previously described by Weishaar et al., Hypertension 15:528, (1990). Briefly, 1–2 units of platelets are suspended in an equal volume of buffer A (20 mM Tris-HCl, pH 7.5, containing 2 mM magnesium acetate, 1 mM dithiothreitol and 5 mM $Na_2EDTA$) using a polytron. The proteinase inhibitor phenylmethylsulfonyl fluoride (PMSF) are also included in this buffer at a final concentration of 200 $\mu$M. This and all subsequent procedures are performed at 0–4° C. The homogenate is then centrifuged at 100,000 rpm for 60 minutes. The supernatant is then removed and filtered through four layers of gauze and applied to a DEAE-Trisacryl M column. The column is washed with several bed volumes of buffer B (20 mM Tris-HCl, pH 7.5, containing 2 mM magnesium acetate, 1 mM diothiothreitol, and 200 $\mu$M PMSF) and eluted by two successive linear NaCl gradients (0.05–0.15 M, 300 ml total; 0.15–0.40 M, 200 ml total). Five ml fractions are collected and assayed for cyclic AMP and cyclic GMP PDE activity. Fractions that contain PDE V are pooled and dialyzed overnight against 4 L of buffer C (20 mM Tris-HCl, pH 7.5, containing 2 mM magnesium acetate and proteinase inhibitors). The dialyzed PDE V is then concentrated to 10% of the original volume, diluted to 50% with ethylene glycol monoethyl ether and stored at −20 C. PDE V can typically be retained for up to four weeks with little or no loss of activity.

Measuring Type V PDE Activity: Enzyme activity are assessed by measuring the hydrolysis of [$^3$H]-cyclic GMP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 uM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range: 0.1, 1, 10, 100 uM (n=1), and $IC_{50}$ determinations are made using 5 appropriate concentrations (n=2).

PDE V INHIBITORY ACTIVITY

| Compound | PDE IV $IC_{50}$ ($\mu$M) |
|---|---|
| 1,3,8-triethyl-2,6-dithioxanthine | 3.2 |
| 1,3,8-triethyl-2-thioxanthine | 26.2 |
| 8-cyclopropyl-1-ethyl-3-(2 methyl-butyl) 6-thioxanthine | 0.1 |
| 1,8-diethyl-3-(2-methyl-butyl)-6-thioxanthine | 0.2 |
| 1,3-diethyl-8-isopropyl- 6-thioxanthine | 1.1 |
| 8-cyclopropyl-1,3-dipropyl-6-thioxanthine | 3.4 |
| 8-isopropyl-1,3-dipropyl-6-thioxanthine | 4.2 |
| 1,3-diethyl-8-cyclopropyl-2,6-dithioxanthine | 4.6 |
| 1-(4-chlorobenzyl)-3-ethyl-8-isopropyl-6-thioxanthine | 0.6 |
| 3-(4-chlorobenzyl)-1-ethyl-8-isopropyl-6-thioxanthine | 0.3 |
| 1,3-Di-(4-chlorobenzyl)-8-isopropyl-6-thioxanthine | 0.1 |
| 3-(3-Cyclopentyloxy-4-methoxy-benzyl)-1-ethyl-8-isopropyl-6-thioxanthine | 3.0 |
| 3-Ethyl-8-isopropyl-1-methyl-6-thioxanthine | 1.0 |
| 8-Cyclopropyl-1,3-diethyl-6-thioxanthine | 1.2 |
| 1,3-dipropyl-8-ethyl-6-thioxanthine | 4.4 |
| 1,8-dimethyl-3-(2-methylbutyl)-6-thioxanthine | 0.1 |

As can be seen from the foregoing, the compositions of the present invention are also potent inhibitors of PDE V in mammals. Such activity is useful in the medical arts to reduce smooth muscle cell proliferation and increase pulmonary vasodilation. In certain aspects of the invention, the compounds demonstrate a combination of selective PDE IV and PDE V inhibition and can be used in diseases such as restenosis and related diseases. Such aspects, of course, include administering an effective amount of a compound of the present invention possessing said combination of PDE IV and V inhibitory activities to a mammal in need of such therapy.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. A pharmaceutical composition comprising at least one pharmaceutically acceptable carrier and a compound selected from the group consisting of 1,3,8-triethyl-2,6-dithioxanthine;
1,3,8-triethyl-2-thioxanthine;
8-cyclopropyl-1-ethyl-3-(2-methyl-butyl)-6-thioxanthine;
1,3-diethyl-8-isopropyl-6-thioxanthine;
8-cyclopropyl-1,3-dipropyl-6-thioxanthine;
8-isopropyl-1,3-dipropyl-6-thioxanthine;
1,3-diethyl-8-cyclopropyl-2,6-dithioxanthine;
1-(4-chlorobenzyl)-3-ethyl-8-isopropyl-6-thioxanthine; and
8-cyclopropyl-1,3-diethyl-6-thioxanthine.

2. A method of effecting PDE IV inhibition which comprises administering to a patient suffering from a disease or disorder selected from the group consisting of asthma, allergies, PDE IV modulated inflammation, and depression, a therapeutically effective amount of a compound selected from the group consisting of 1,3,8-triethyl-2,6-dithioxanthine;
1,3,8-triethyl-2-thioxanthine;
8-cyclopropyl-1-ethyl-3-(2-methyl-butyl)-6-thioxanthine;
1,3-diethyl-8-isopropyl-6-thioxanthine;
8-cyclopropyl-1,3-dipropyl-6-thioxanthine;
8-isopropyl-1,3-dipropyl-6-thioxanthine;
1,3-diethyl-8-cyclopropyl-2,6-dithioxanthine;
1-(4-chlorobenzyl)-3-ethyl-8-isopropyl-6-thioxanthine; and
8-cyclopropyl-1,3-diethyl-6-thioxanthine.

3. A compound selected from the group consisting of:
1,3,8-triethyl-2,6-dithioxanthine;
1,3,8-triethyl-2-thioxanthine;
8-cyclopropyl-1-ethyl-3-(2-methyl-butyl)-6-thioxanthine;
1,3-diethyl-8-isopropyl-6-thioxanthine;
8-cyclopropyl-1,3-dipropyl-6-thioxanthine;
8-isopropyl-1,3-dipropyl-6-thioxanthine;
1,3-diethyl-8-cyclopropyl-2,6-dithioxanthine;
1-(4-chlorobenzyl)-3-ethyl-8-isopropyl-6-thioxanthine; and
8-cyclopropyl-1,3-diethyl-6-thioxanthine.

4. The compound of claim 3 which is 1,3,8-triethyl-2,6-dithioxanthine.

5. The compound of claim 3 which is 1,3-diethyl-8-isopropyl-6-thioxanthine.

6. The compound of claim 3 which is 8-cyclopropyl-1,3-dipropyl-6-thioxanthine.

7. The compound of claim 3 which is 8-isopropyl-1,3-dipropyl-6-thioxanthine.

8. The compound of claim 3 which is 1,3-diethyl-8-cyclopropyl-2,6-dithioxanthine.

9. The compound of claim 3 which is 1-(4-chlorobenzyl)-3-ethyl-8-isopropyl-6-thioxanthine.

10. The compound of claim 3 which is 8-cyclopropyl-1,3-diethyl-6-thioxanthine.

11. The compound of claim 3 which is 8-cyclopropyl-1-ethyl-3-(2-methyl-butyl)-6-thioxanthine.

12. The compound of claim 3 which is 1,3,8-triethyl-2-thioxanthine.

13. A method of effecting PDE IV inhibition which comprises administering to a patient suffering from a disease or disorder selected from the group consisting of asthma, allergies, depression and rhinitis, a therapeutically effective amount of a compound selected from the group consisting of 1,8-diethyl-3-(2-methylbutyl)-6-thioxanthine;
3-ethyl-1-methyl-8-isopropyl-6-thioxanthine;
1,3-dipropyl-8-ethyl-6-thioxanthine; and
1,8-dimethyl-3-(2-methylbutyl)-6-thioxanthine.

* * * * *